United States Patent [19]
Gray et al.

[11] Patent Number: 5,401,966
[45] Date of Patent: Mar. 28, 1995

[54] SPECTROPHOTOMETRIC SENSOR ASSEMBLY INCLUDING A MICROLAMP

[75] Inventors: Damien F. Gray, Mt. View; Richard J. Pittaro, San Carlos; Paul K. Lum, Los Altos, all of Calif.

[73] Assignee: Hewlett-Packard Company, Palo Alto, Calif.

[21] Appl. No.: 115,535

[22] Filed: Sep. 2, 1993

[51] Int. Cl.⁶ .......................................... G01N 21/61
[52] U.S. Cl. ................... 250/343; 250/339.13
[58] Field of Search ............. 250/343, 339.13, 339.02, 250/495.1

[56] References Cited

U.S. PATENT DOCUMENTS

| | | | |
|---|---|---|---|
| 4,648,396 | 3/1987 | Raemer | 128/204.22 |
| 5,134,302 | 7/1992 | Rosenthal | 250/504 R |
| 5,153,436 | 10/1992 | Apperson et al. | 250/345 |
| 5,159,199 | 10/1992 | LaBaw | 250/339.02 |

OTHER PUBLICATIONS

Solomon, Rodney J. "A Reliable, Accurate $CO_2$ Analyzer for Medical Use," (Sep. 1981) *Hewlett-Packard Journal* pp. 3-21.

Mastrangelo, Carlos H. et al. "Electrical and Optical Characteristics of Vacuum-Sealed Polysilicon Microlamps," *IEEE Transactions On Electron Devices*, vol. 39, No. 6, (Jun. 1992) pp. 1363-1375.

*Primary Examiner*—Constantine Hannaher

[57] ABSTRACT

A spectrophotometric sensor assembly that may find particular use in a capnometer, a medical device for measuring the concentration of carbon dioxide in the exhaled breath of a patient, includes at least one microlamp. A microlamp is a very small source of electromagnetic radiation including a heated filament disposed over a substrate. The microlamp may be constructed using semiconductor fabrication techniques. The microlamp typically emits broad-band infrared radiation. Radiation from the microlamp usually passes through a filter, which preferentially transmits radiation of a preselected wavelength. The radiation then passes through a sample chamber and onto a detector. The concentration of a substance of interest within the chamber may be computed by determining the degree to which the radiation is absorbed in the chamber. In a preferred embodiment, an array of microlamps is sequentially triggered in a rapid manner.

25 Claims, 4 Drawing Sheets

SPECTROPHOTOMETRIC SENSOR ASSEMBLY INCLUDING A MICROLAMP

BACKGROUND OF THE INVENTION

1. Field of the Invention

The present invention relates generally to apparatus for the determination of the composition of a sample by spectrophotometry. More particularly, the invention provides a sensor assembly including one or more microlamps fabricated onto a semiconductor chip. Such a sensor assembly may find particular use in a capnometer, a medical device for measuring carbon dioxide content in the exhaled breath of a patient, especially one whose breathing is controlled by a mechanical ventilator.

2. Description of the Background Art

Carbon dioxide ($CO_2$) is produced in the body as a normal byproduct of human metabolism. Gaseous $CO_2$ is eliminated from the body through the lungs in exhaled breath. The concentration of $CO_2$ carried by blood in the arteries is the primary stimulus for respiratory control. Normally, if $CO_2$ builds up in the blood, the body's regulatory functions increase the breath rate until the $CO_2$ concentration returns to a normal level.

In a patient breathing with the assistance of a mechanical ventilator, however, the patient's breath rate is controlled by the machine. Should $CO_2$ begin to accumulate in the blood, the ventilator controls must be adjusted to restore the $CO_2$ concentration to an acceptable level. Although the blood $CO_2$ level may be measured directly, e.g., by blood gas analysis, it is usually preferable to monitor the concentration of $CO_2$ in the patient's exhaled breath. Breath monitoring allows adjustments to be made almost immediately, compared with a delay of at least several minutes with blood-gas analysis.

Instruments for the measurement of $CO_2$ concentration in the exhaled breath of a patient are known in the medical arts. These devices are called "capnometers," from Greek, kapnos, for "smoke." One such instrument has been available as the Hewlett-Packard Model 47210A Capnometer. This device is described in Solomon, R. J., "A Reliable, Accurate $CO_2$ Analyzer for Medical Use," *Hewlett-Packard Journal*, September 1981, pp. 3-21.

The 47210A system uses spectrophotometry to measure the $CO_2$ level in a patient's exhaled breath. Radiation from an infrared source is transmitted through a gas sample chamber through which exhaled air passes. Radiation from the source is partially absorbed as it passes through the gas sample. The degree of absorption is strongly dependant upon wavelength but for a given wavelength the degree of absorption is directly related to the concentration of $CO_2$ present in the sample. By passing radiation of a preselected wavelength known to be strongly absorbed by $CO_2$ through a sample tube containing air exhaled by the patient, and by determining the amount of radiation absorbed by the sample, the concentration of $CO_2$ in the patient's exhaled breath can be conveniently determined with a high degree of precision.

FIG. 1 depicts the infrared radiation source used in the Model 47210A capnometer. Infrared source 10 includes a glow bar 15 connected to a pair of current leads 17 and 18. The glow bar is disposed in front of an ellipsoidal mirror 20 inside a transistor can 23. Glow bar 15 is formed of a resistive ceramic-metal composite (cermet) material. When current flows through the glow bar, electrical resistance heats the glow bar, causing it to emit infrared radiation across a broad band of wavelengths. This radiation is focused and directed outwardly from source 10, through a sapphire window 25 by mirror 20.

From infrared source 10, the infrared radiation is directed through a sample chamber 30 as depicted in FIG. 2. The sample chamber is a tube through which passes breath exhaled by the ventilated patient. Sample chamber 30 should be located as near as possible to the patient so that measurement of $CO_2$ in the sample can be made immediately as the breath leaves the patient. For this reason, the sample chamber is preferably formed as a part of an airway adapter 32, through which the patient is ventilated.

The sample chamber 30 may, however, also be located away from the patient, with a sample line going to the patient's airway. The disadvantage of such a "sidestream" configuration is that there is typically a delay of several seconds and some smoothing of the waveforms, but neither of these problems is significant in most clinical settings.

A rotating filter wheel 33 is disposed between sample chamber 30 and an infrared detector 35. Filter wheel 33, driven by a motor drive (not shown), serves two important functions. First, the filter wheel includes three individual elements through which radiation is transmitted. Two of these elements are sealed gas cells 37 and 38. One cell contains a reference gas sample containing a known concentration of $CO_2$; the other cell holds only nitrogen. A third element is an opening 40, a hole in the filter wheel, through which radiation passes unimpeded. Finally, the material of the filter wheel in an area 42 opposite opening 40 is opaque to radiation from source 10.

Infrared source 10, filter wheel 33, and detector 35 are housed inside a sensor housing 44, which clips onto airway adapter 32 over sample chamber 30. The concentration of $CO_2$ within sample chamber 30 is computed by comparing the intensity of radiation impinging on detector 35 when each of wheel elements 37, 38, 40, and 42 lies between source 10 and the detector. The filter wheel in the 47210A unit rotates at 2400 rpm. Thus, forty measurements per second can be taken through a given element (open cell, reference cell, or opaque region).

The second function of the filter wheel is to serve as a mechanical shutter to "chop" the radiation into discrete on and off periods. The detector is exposed to radiation from the source only during the time when a transmissive filter element is passing in front of the source. At other times, the radiation is prevented from reaching the detector.

The "off" periods during which radiation is blocked allow the detector to settle to a zero intensity rest state. If the detector were exposed to radiation continually, the measurements would be subject to errors induced by electronic "drift" in the detector and the system electronics. Conceivably, off periods could be provided simply by switching off the current flowing through the glow bar. However, the relatively high thermal mass (mass times specific heat) of the glow bar means that a relatively long period of time would be required for the glow bar to cool. The glow bar could certainly not be switched on and off nearly as rapidly as is provided by the rotating filter wheel.

While capnometers such as the Model 47210A described above have found widespread use in the medical industry, further improvements are possible. For example, it would be desirable if the size and weight of the sensor assembly could be reduced so that placement of the sensor assembly near the patient would be more convenient. First, there is less unwanted smoothing of the signal waveforms when the instrument has a smaller sample volume (dead volume); although this problem is not as severe for adult patients as for children, it is a critical problem for neonatal patients. Second, conventional capnometers such as the Model 47210A are so heavy that they can tear the breathing tube out of neonatal patients.

It would also be desirable if the rotating filter wheel and its associated drive motor could be eliminated. This would further reduce the weight and bulk of the sensor assembly and enhance the simplicity and reliability of the entire system.

SUMMARY OF THE INVENTION

The invention described herein provides a spectrophotometric sensor assembly that may find particular use in a capnometer, a medical device for measuring the concentration of carbon dioxide in the exhaled breath of a patient. According to the invention, the sensor assembly includes at least one microlamp. The microlamp serves as a source of blackbody electromagnetic radiation, which is generally concentrated in the infrared band.

The microlamp includes a small filament disposed over a substrate. Infrared radiation is emitted from the filament when the filament is heated by current flowing through it. The microlamp and filament are constructed using techniques similar to those used in the fabrication of semiconductor chips. The microlamp usually has a filter disposed over it. The filter preferentially transmits radiation of a predetermined wavelength. In a capnometer, this predetermined wavelength may advantageously be approximately 4.3 micrometers, a wavelength that is strongly absorbed by carbon dioxide.

From the microlamp, the radiation passes through a sample chamber containing a quantity of the patient's exhaled breath. The radiation will usually be directed through the sample chamber by an optical assembly that in a preferred embodiment comprises a pair of spherical mirrors. The radiation then impinges upon a detector, which measures the amount of radiation transmitted through the chamber and the sample held inside it.

Preferred embodiments will include a plurality of microlamps and associated filters. In multiple microlamp embodiments, one of the microlamps will generally be associated with a filter that preferentially transmits radiation having a wavelength that is not strongly absorbed by any substance expected to be found within the sample. Radiation from this microlamp is used as a reference.

Other microlamps may be associated with filters preferentially transmitting radiation having different wavelengths. These wavelengths are generally chosen to correspond to various constituents other than carbon dioxide expected to be found in the breath sample. Alternatively, two or more microlamps may have filters that preferentially transmit substantially the same wavelength so that the second microlamp can be switched on as a back-up in case the first one fails.

DETAILED DESCRIPTION

This invention provides an improved sensor assembly that may find particular use in a spectrophotometric capnometer. The sensor assembly uses a source module in which one or more microlamps are used as a source of radiation. The radiation will typically be concentrated in the infrared portion of the electromagnetic spectrum.

In a microlamp, a tiny filament, usually formed of polysilicon, but sometimes of a metal such as tungsten, is formed on a silicon wafer substrate using semiconductor fabrication techniques. See, for example, "IC-Processed Hot-Filament Vacuum Microdevices," Kirt R. Williams and Richard S. Muller, submitted as an abstract at the IEEE International Electron Devices Meeting (IEDM '92), 13–16 December 1992. Such a microlamp can be described as an "integrated filament" microlamp because it is fabricated using techniques similar to those used to manufacture integrated circuits on silicon wafer "chips." Some characteristics of one type of integrated filament microlamp are described in Mastrangelo, Carlos H., James Hsi-Jen Yeh, and Richard S. Muller, "Electrical and Optical Characteristics of Vacuum-Sealed Polysilicon Microlamps," *IEEE Transactions on Electron Devices*, Vol. 39, No. 6, June 1992, pp 1363–75.

Figure 1:
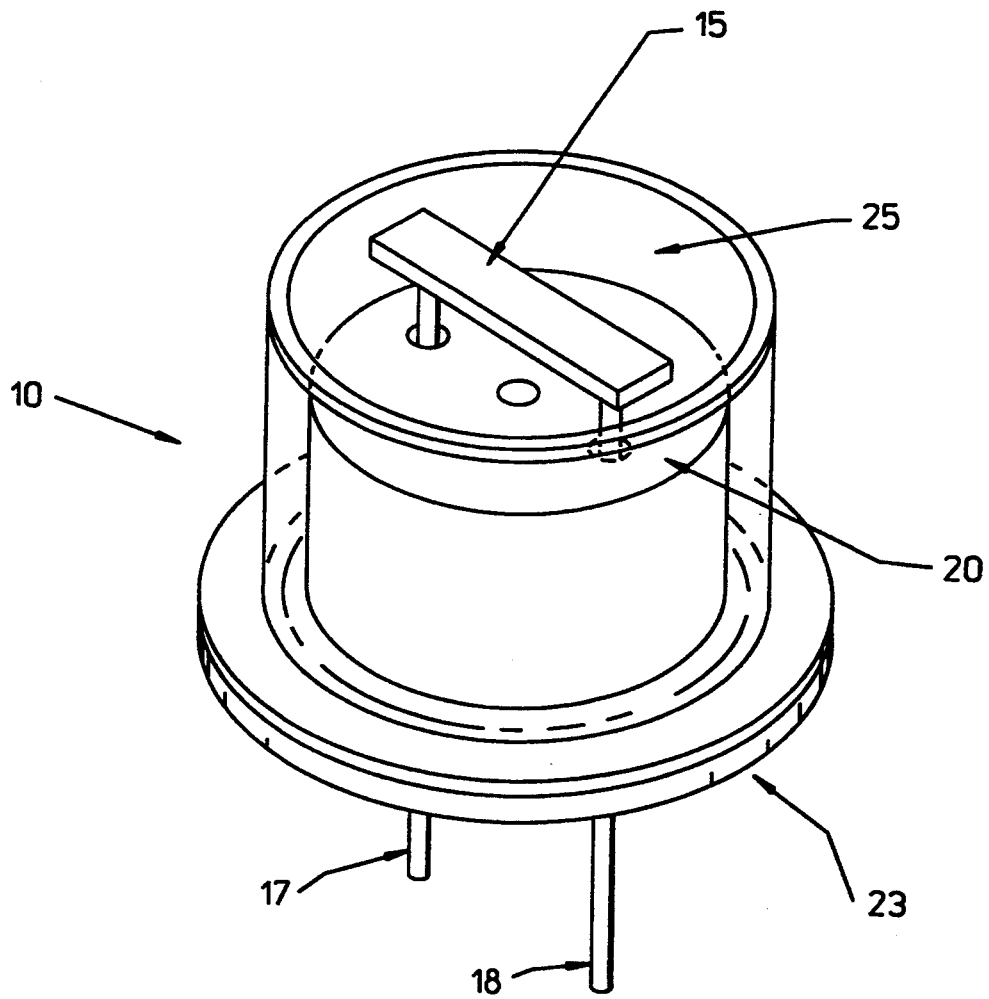
FIG. 1 depicts an infrared source used in a prior art sensor assembly.
Figure 2:
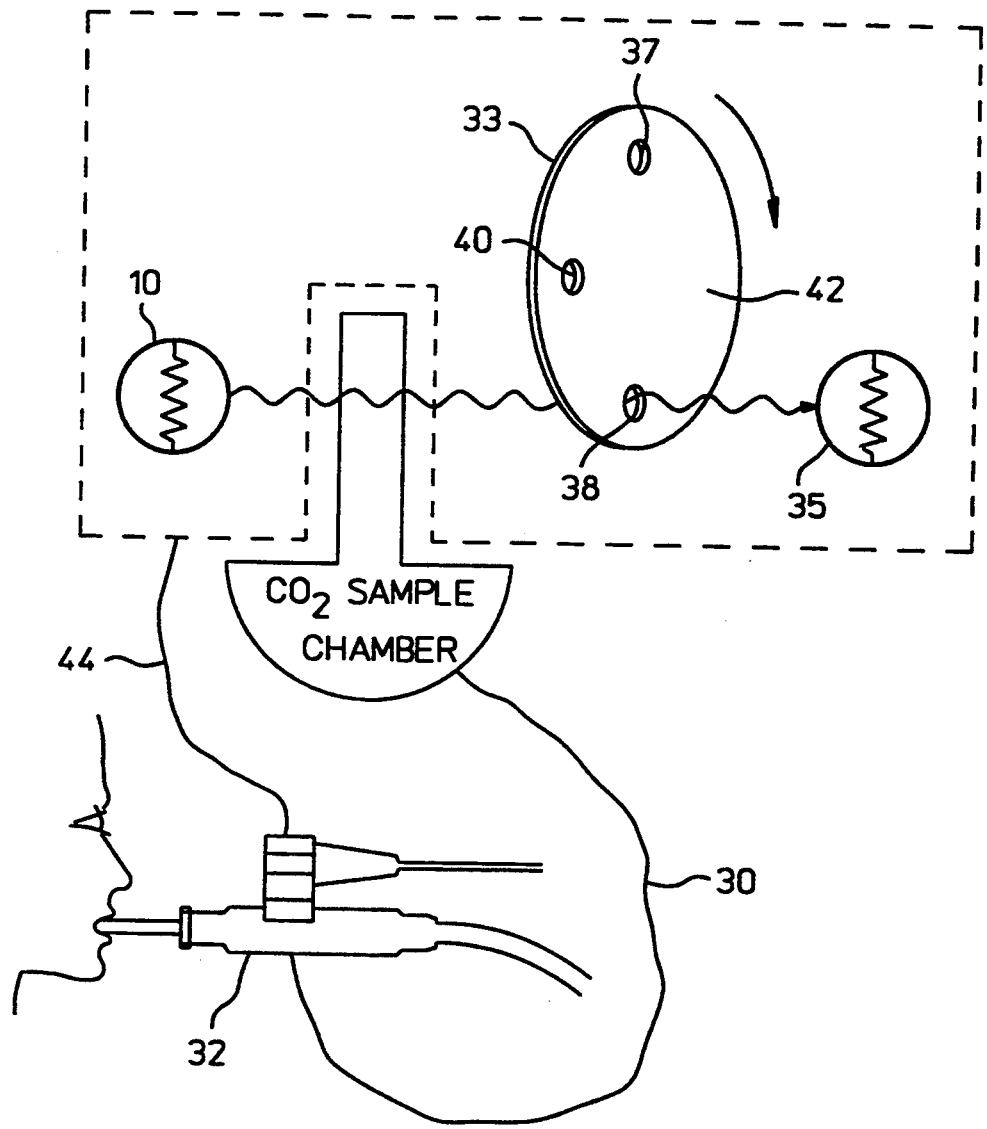
FIG. 2 is a schematic depiction of a prior art sensor assembly including a rotating filter wheel.
Figure 3:
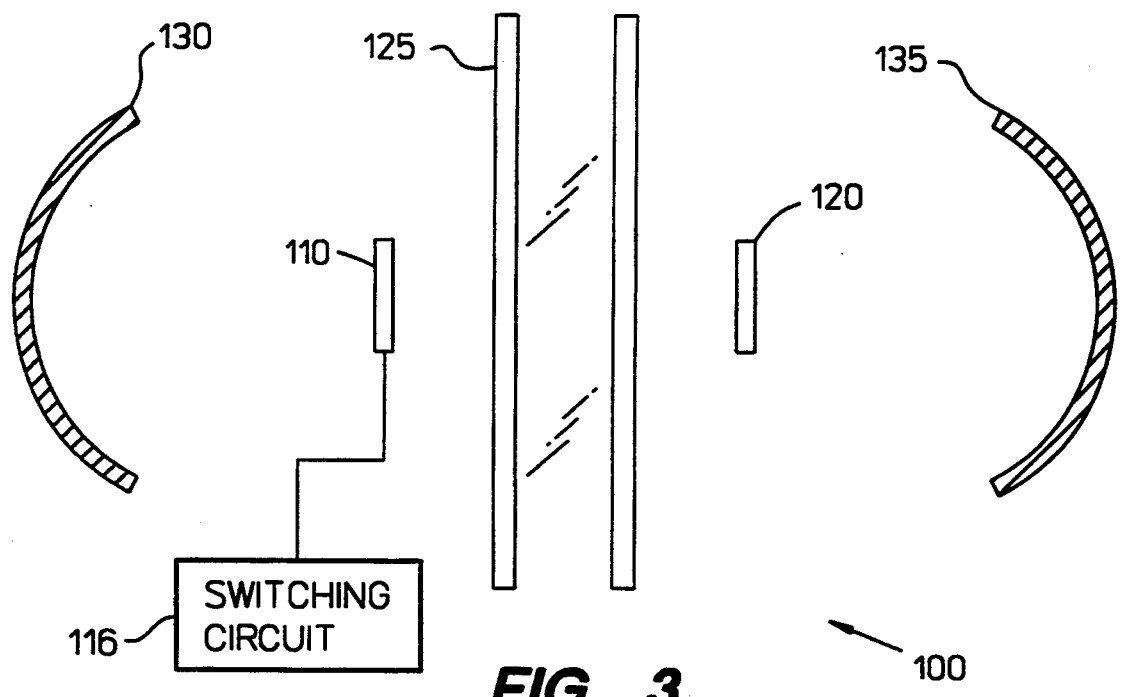
FIG. 3 depicts an embodiment of a sensor assembly according to the present invention.

A capnometer sensor assembly is depicted in FIG. 3. Sensor assembly 100 comprises a source module 110, a detector 120, and an optical assembly. The optical assembly directs radiation from source module 110 through a sample chamber 125 and onto detector 120. Sample chamber 125 typically forms a part of the airway through which expired breath from a patient flows as was the case in the prior art embodiment described above. The walls of the sample chamber are transparent to radiation (typically infrared) emitted from the source module.

In the embodiment depicted, the optical assembly comprises first and second spherical mirrors 130 and 135. Spherical mirrors 130, 135 are generally about ten to fifteen millimeters in radius, which corresponds roughly to the size of a standard breathing tube; the actual sizes in a given application may vary, however, and will depend on the design needs of the particular application. The source module and detector are each preferably located about two radii (that is, at the focal points of the spherical mirrors 130, 135), away from the surface of the first and second mirror, respectively. This configuration disperses radiation from the source module through a wide area of the sample chamber before refocusing a portion of the transmitted radiation onto the detector. This reduces the effect of small irregularities, for example, particulate contamination, on the walls of the sample chamber.

Spherical mirrors are preferred because they are readily available, easily manufactured, and cheaper. Other configuration are possible, however. For example, parabolic mirrors (both on- and off-axis) may also be used to provide a more parallel light beam through the sample volume and better imaging near the focus on the detectors. Confocal elliptical mirrors, which collect more light from a greater solid angle, may provide a better throughput of light. A single elliptical mirror may also be used, since it has two focii—the source and detector are thereby preferably located at a respective focus of the mirror, with the source at the focus closest the mirror to provide greater light collection. Such parabolic or elliptical mirrors could be made using any known manufacturing method such as by being turned, electroformed, or cast; the choice of method will depend on the image quality needed in a particular application and the cost involved.

The detector may be of any conventional type suitable for detecting radiation emitted by the source module. For example, a lead-selenide photoresistor may be used for $4.3\mu$ radiation detection of $CO_2$. Other alternative detectors include HgCdTe and pyroelectric LiTaO$_3$ detectors. A lead-selenide is preferred, however, because, at room temperature (the approximate normal operating environment of the instrument), it has less noise.

Figure 4:
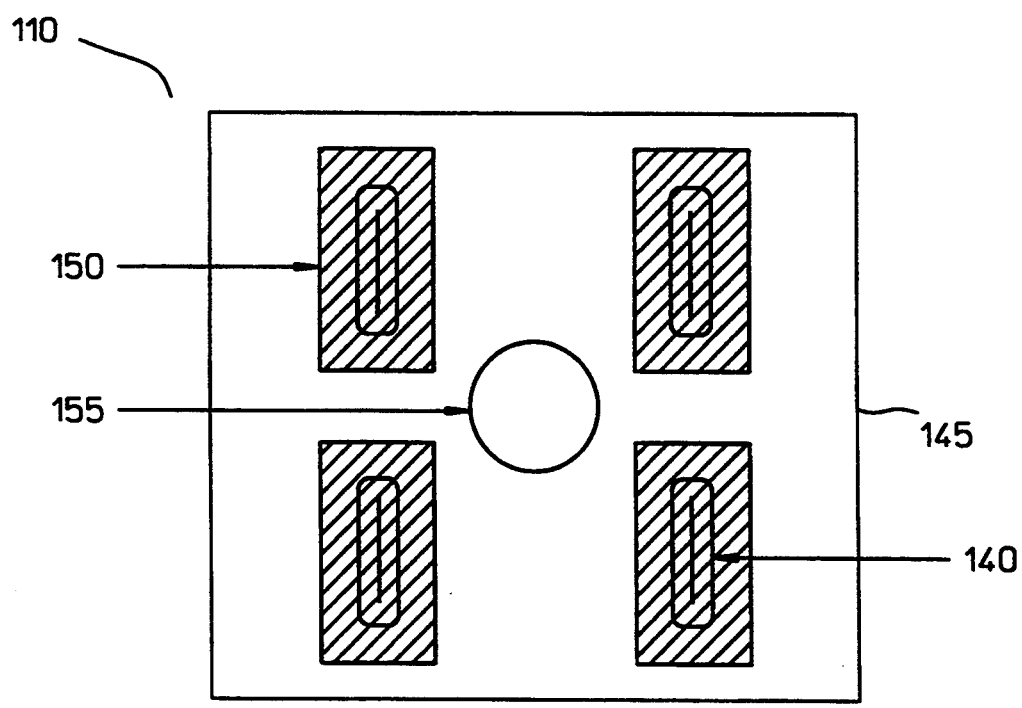
FIG. 4 is a top view of a source module including a plurality of individually filtered microlamps suitable for use in a sensor assembly according to the present invention.

A source module is depicted in FIG. 4. FIG. 4 shows a top view of the source module, the view that would be seen from the surface of first mirror 130 in FIG. 3. As depicted therein, source module 110 has a plurality of individual microlamps 140. Each microlamp includes a filament disposed over a groove (typically V-shaped when using conventional etching techniques), in the surface of a base 145. The filaments are typically on the order of a few hundred micrometers long and a few micrometers wide. The filaments are generally formed of polysilicon. Alternatively, microlamp filaments may be formed of small strands of tungsten or another suitable metal.

Each microlamp 140 has an associated optical filter 150 disposed over it. The filters are typically fastened with epoxy to the base. The filters could also be evaporated directly onto the base over the microlamps but this requires careful control to achieve acceptable filters of precise thickness.

Each filter is designed to preferentially transmit radiation having a preselected wavelength so that the filter functions as a "band pass" filter. The preferred wavelength can be preselected by modifying the filter according to known techniques, e.g., by changing the thickness or the refractive index of the filter material. The filters associated with different filaments are selected to preferentially transmit radiation having different wavelengths. In a capnometer, it is advantageous for one of the filters to preferentially transmit radiation having a wavelength of about 4.3 micrometers because radiation of this wavelength is strongly absorbed by carbon dioxide.

Other filters are formulated to preferentially transmit radiation having wavelengths strongly absorbed by other substances expected to be found in expired breath, e.g., $H_2O$ or $N_2O$. Additionally, one of the filters is usually selected to transmit radiation having a wavelength that is not absorbed by any substance expected to be found in human breath. Radiation of this wavelength serves as a reference for comparison with radiation having the other, absorbed, wavelengths. The selection of preferred wavelengths for absorption and reference will be familiar to those skilled in the measurement of gas composition by spectrophotometry.

The microlamps are actuated sequentially using conventional switching circuitry 116 so that only one filament radiates infrared energy at a given time. Rapid switching of the microlamps is feasible because the thermal mass of the filaments is much less than the thermal mass of the glow bar previously used. Consequently, the microlamp filaments can heat up when switched on and cool down when switched off very rapidly.

In this invention, rapid switching takes the place of the chopping function performed by the transparent elements of the rotating filter wheel used in devices found in the prior art. Using the invention it is not, moreover, necessary for the microlamps to be turned completely off in the "off" state; rather, especially since the activation signal to the microlamps will in many applications be AC coupled, it will often be fully sufficient for modulation just to turn the lamps down to a quiescent (but not null) low state.

Furthermore, the sealed gas reference cells previously found on the rotating filter wheel are no longer needed because each of the microlamps is individually filtered. In the previous system, sealed gas cells containing gas samples having known $CO_2$ concentrations were used as reference cells. In contrast, the present system dispenses with the reference cells. Instead, one of the microlamps is filtered to produce a narrow band radiation of a preselected wavelength to serve as a reference.

The small size and low mass of the microlamps are inherently advantageous because it is desirable for the measurement sensor to be made as compact and lightweight as possible so that it may be conveniently attached to the airway near the patient. Furthermore, the use of a plurality of individually switched and filtered infrared sources eliminates the need for the filter wheel and the associated drive motor used in the previous design. In addition to making the unit even more light and compact, eliminating the rotating parts simplifies the device considerably, thereby increasing the reliability of the system.

Referring again to FIG. 4, a photodetector 155 may be disposed on base 145 in close proximity to the microlamps 140. This photodetector detects radiation directly from the microlamps and so is available to monitor the power output from the microlamps. Power monitoring photodetector 155 should not be confused with primary infrared detector 120 (FIG. 3), which detects radiation transmitted through the sample. Note that silicon photodetectors detect in the 0.4–1.0 $\mu$ region and that the source, which acts roughly as a black body, emits energy in this region.

Although FIG. 4 depicts a relatively simple embodiment comprising only four microlamps, more microlamps might be used. Samples have been fabricated that include about fifty individual microlamps on a square chip about four millimeters on a side. If more microlamps were included on the source module, these microlamps could be paired with filters having other preferred wavelengths to allow for more complex measurements.

Figure 5:
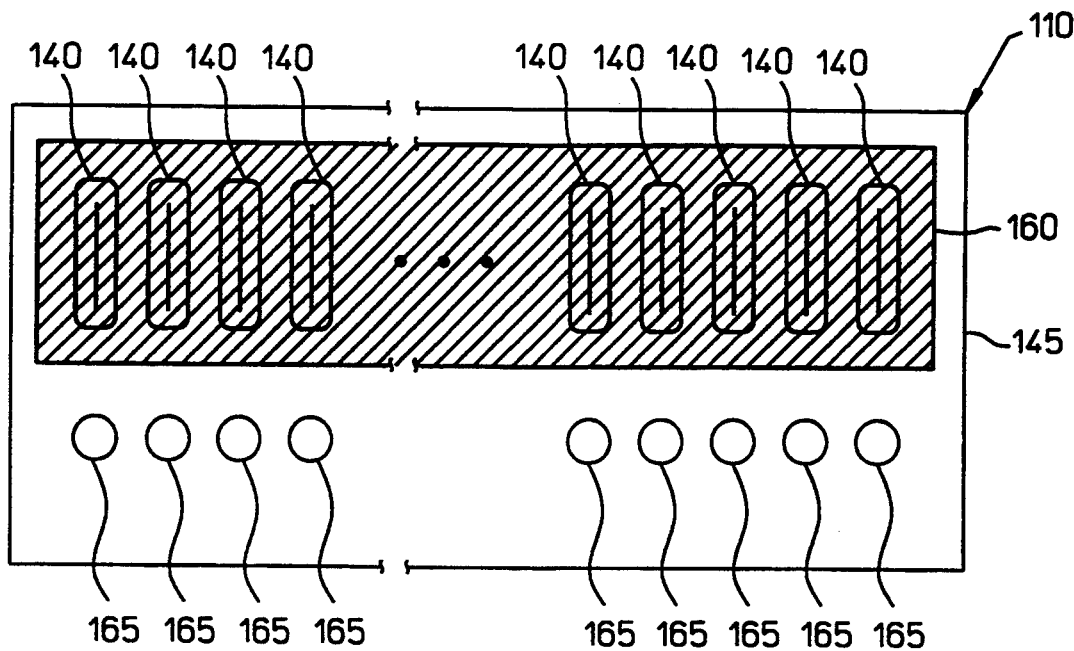
FIG. 5 illustrates a multi-microlamp, multiple-reference detector embodiment of the source module.

FIG. 5 illustrates an embodiment of the invention in which several microlamps 140 are mounted on the base 45. The light emitted from each microlamp is then filtered before it reaches the detector. The filtering can be done either with separate filters or a single filter. If separate filters are used, they may all have different transmission frequencies, or certain microlamp/filter combinations could be made equivalent to provide a back-up capability (for example by mounting the same filter over more than one microlamp).

If a single filter is used, it may be mounted over all (or at least most, if one or more microlamps are to remain unfiltered to provide a test or control) of the microlamps. In the embodiment shown in FIG. 5, all the microlamps 140 are mounted under a single linearly variable filter 160. Suitable linearly variable filters can be fabricated using known techniques and are commercially available, for example, from Optical Coating Laboratory, Inc., of Santa Rosa, Calif., USA. In this case, the different portions of the linearly variable filter 160 over the respective microlamps act as separate filters, but the single filter element is more easily manufactured and mounted.

The series of microlamps 140 is switched on in sequence (using any conventional switching or multiplexing circuitry), to electronically sweep the radiation across a broad band of wavelengths. As before, one or more detectors 165 are mounted on the base 145 to sense the strength of energy at the different wavelengths.

Alternatively, the additional microlamps could serve as backups for the primary microlamps. If a given microlamp were to fail, a backup microlamp paired with a filter of the same frequency could be switched on by conventional control circuitry to replace the failed lamp. Other applications using a large number of microlamps on a single chip may be desirable as well.

Figure 6:
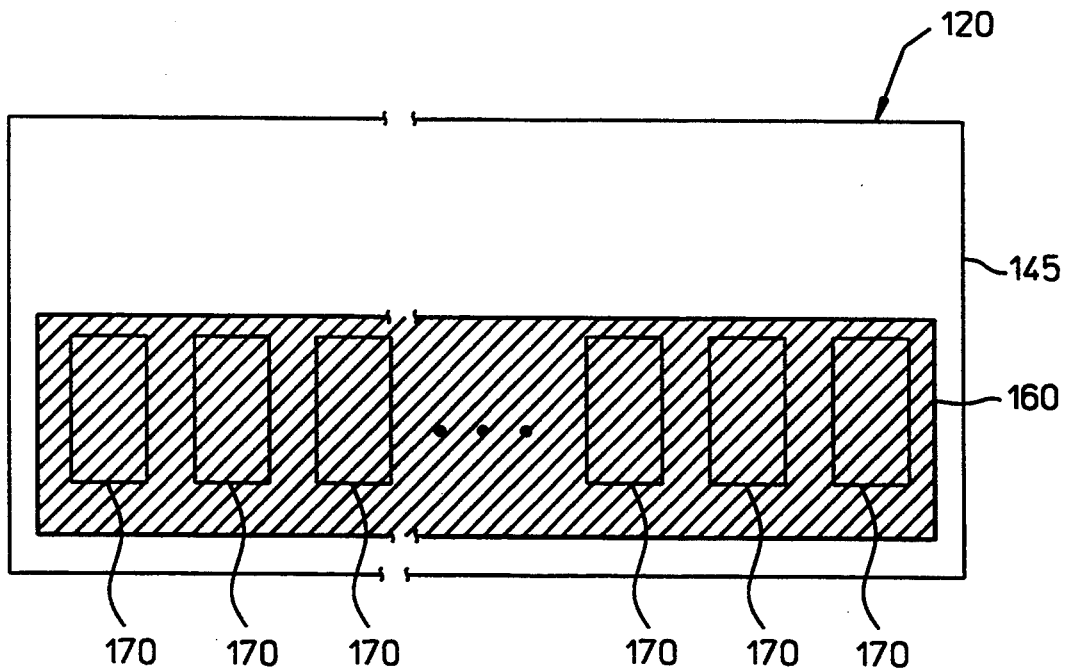
FIG. 6 illustrates a multi-detector embodiment of a detector module.

The embodiment shown in FIG. 5 has a number of individually filtered microlamps 140 and power monitoring detectors 165. Other combinations of microlamps, filters, and detectors are possible as well. For example, a linear detector array (composed of many detectors 170), such as that shown in FIG. 6, could be used. A linearly variable filter 160 is placed over the detector array if a single microlamp is used as a source. Alternatively, the linear array of microlamps in FIG. 5 could be used as a source with the microlamps imaged 1:1 onto the detector array. The linearly variable filter is then placed over either the microlamp array or the detector array.

What is claimed is:

1. A sensor assembly for monitoring content of a gas of interest within exhaled breath of a person comprising:
   a source of radiation selected such that the gas of interest is absorptive of the radiation, the source including an integrated filament microlamp;
   an airway adapter for connection to a passageway of exhaled breath, the airway adapter having a sample chamber; and
   a detector disposed to detect radiation from the microlamp that has traversed the sample chamber.

2. The sensor assembly of claim 1, further comprising an optical assembly disposed to direct radiation from the microlamp through the sample chamber onto the detector.

3. The sensor assembly of claim 2, wherein the optical assembly comprises at least one mirror.

4. The sensor assembly of claim 3, wherein the optical assembly comprises at least one spherical mirror.

5. The sensor assembly of claim 4, wherein the optical assembly comprises a pair of spherical mirrors and wherein the microlamp and the detector are positioned between the mirrors.

6. The sensor assembly of claim 1, further comprising a filter disposed along the path of radiation travelling from the microlamp to the detector, the filter preferentially transmitting radiation of a preselected wavelength.

7. The sensor assembly of claim 6, wherein the filter is disposed over the microlamp.

8. The sensor assembly of claim 6, wherein the filter preferentially transmits radiation having a wavelength of approximately 4.3 micrometers.

9. The sensor assembly of claim 1, further comprising a photodetector disposed so that radiation from the microlamp impinges directly on the photodetector without traversing the sample chamber.

10. A sensor assembly according to claim 1, further including:
    a plurality of integrated filament microlamps; and
    a plurality of filters disposed over the microlamps;
    in which:
    the detector is disposed to detect radiation from the plurality of microlamps that has traversed the sample chamber.

11. The sensor assembly of claim 10, wherein the filters preferentially transmit radiation having different wavelengths.

12. The sensor assembly of claim 11, in which the filters are formed as portions of a single linearly variable filter element.

13. The sensor assembly of claim 10, wherein at least two of the filters preferentially transmit radiation having substantially the same wavelength.

14. The sensor assembly of claim 10, wherein the microlamps and filters are disposed on a common source module in the form of a silicon chip.

15. The sensor assembly of claim 10 further comprising means for rapid sequential switching of said plurality of microlamps.

16. The sensor assembly of claim 15 wherein said means for rapid sequential switching is a switching circuit connected to said microlamps to control activation such that only one microlamp radiates at a given time.

17. A sensor assembly according to claim 1, further including:
    a plurality of detectors disposed to detect radiation from the microlamp that has traversed the sample chamber; and
    a plurality of filters disposed over the detectors;
    in which:
    all of the detectors are disposed to detect radiation from the microlamp that has traversed the sample chamber.

18. The sensor assembly of claim 17, wherein the filters preferentially transmit radiation having different wavelengths.

19. The sensor assembly of claim 18, in which the filters are formed of portions of a single linearly variable filter element.

20. The sensor assembly according to claim 1, further including:
    a plurality of microlamps;
    a plurality of detectors disposed to detect radiation from the plurality of microlamps and that has traversed the sample chamber; and a linearly variable filter in the radiation path.

21. The sensor assembly of claim 20, in which the microlamps are imaged 1:1 onto the detectors.

22. The sensor assembly of claim 21, in which the microlamps and the detectors are arranged as a linear array.

23. The sensor assembly of claim 22, in which the linearly variable filter is disposed over the microlamps.

24. The sensor assembly of claim 22, in which the linearly variable filter is disposed over the detectors.

25. The sensor assembly of claim 1 wherein said detector is a lead-selenium detector.

* * * * *